US009918475B2

(12) United States Patent
Moros et al.

(10) Patent No.: US 9,918,475 B2
(45) Date of Patent: *Mar. 20, 2018

(54) ANTI-MICROBIAL COATING AND METHOD TO FORM SAME

(71) Applicant: Allied BioScience, Inc., Dallas, TX (US)

(72) Inventors: Daniel Moros, New York, NY (US); Craig Grossman, Point Roberts, WA (US)

(73) Assignee: ALLIED BIOSCIENCE, INC., Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/041,974

(22) Filed: Feb. 11, 2016

(65) Prior Publication Data

US 2016/0262398 A1 Sep. 15, 2016

Related U.S. Application Data

(63) Continuation-in-part of application No. 14/932,840, filed on Nov. 4, 2015, now Pat. No. 9,856,360.

(60) Provisional application No. 62/114,998, filed on Feb. 11, 2015.

(51) Int. Cl.
| C09D 183/00 | (2006.01) |
| A01N 55/00 | (2006.01) |
| A01N 59/16 | (2006.01) |
| A61L 2/00 | (2006.01) |
| C09D 5/14 | (2006.01) |
| A01N 25/02 | (2006.01) |
| A01N 33/08 | (2006.01) |
| B05D 1/02 | (2006.01) |
| B05D 7/14 | (2006.01) |
| B05D 7/00 | (2006.01) |
| C09D 179/02 | (2006.01) |
| C23C 26/00 | (2006.01) |
| C09D 183/08 | (2006.01) |
| C08K 3/22 | (2006.01) |

(52) U.S. Cl.
CPC ............ *A01N 55/00* (2013.01); *A01N 25/02* (2013.01); *A01N 33/08* (2013.01); *A01N 59/16* (2013.01); *A61L 2/00* (2013.01); *B05D 1/02* (2013.01); *B05D 7/14* (2013.01); *B05D 7/544* (2013.01); *C09D 5/14* (2013.01); *C09D 179/02* (2013.01); *C23C 26/00* (2013.01); *C08K 3/22* (2013.01); *C08K 2003/2241* (2013.01); *C09D 183/00* (2013.01); *C09D 183/08* (2013.01)

(58) Field of Classification Search
CPC ....... C09D 5/17; C09D 183/00; C09D 183/08
USPC ................................................. 106/287.11
See application file for complete search history.

(56) References Cited

U.S. PATENT DOCUMENTS

| 3,068,199 | A | | 12/1962 | Sellers | |
| 3,133,108 | A | | 5/1964 | Finestone | |
| 4,005,025 | A | | 1/1977 | Kinstedt | |
| 4,048,206 | A | * | 9/1977 | Voronkov | ............... A01N 55/00 556/405 |
| 4,740,538 | A | * | 4/1988 | Sekutowski | ........... C08K 3/346 106/487 |
| 5,359,104 | A | | 10/1994 | Higgs et al. | |
| 5,879,436 | A | | 3/1999 | Kramer | |
| 5,945,555 | A | * | 8/1999 | Yoshitake | ............. C07F 7/1836 528/15 |
| 5,954,869 | A | | 9/1999 | Elfersy | |
| 7,704,561 | B2 | | 4/2010 | Mehta et al. | |
| 8,951,341 | B2 | * | 2/2015 | Jaffrennou | ........... C03C 25/146 106/217.7 |
| 2003/0101898 | A1 | | 6/2003 | Standke | |
| 2006/0142459 | A1 | | 6/2006 | Goebel | |
| 2008/0131594 | A1 | | 6/2008 | Cho | |
| 2009/0030220 | A1 | | 1/2009 | Uchibori | |
| 2010/0029530 | A1 | | 2/2010 | Whiteley | |
| 2010/0234506 | A1 | * | 9/2010 | Elizalde | ................ C08F 220/06 524/388 |
| 2012/0015200 | A1 | | 1/2012 | Ali | |
| 2013/0040078 | A1 | | 2/2013 | Scharfe et al. | |
| 2013/0167754 | A1 | | 7/2013 | Wassmer | |
| 2014/0158018 | A1 | | 6/2014 | Geoffrion et al. | |
| 2015/0020712 | A1 | * | 1/2015 | Wosylus | ............... C09C 1/0021 106/457 |

FOREIGN PATENT DOCUMENTS

| CN | 103305029 | | 9/2013 |
| CN | 103351916 | * | 10/2013 |
| JP | 06287068 | | 5/2012 |
| RU | 2450516 | | 10/1994 |
| SU | 1130570 | | 12/1984 |
| SU | 1567314 | | 5/1990 |
| WO | 2012142621 A1 | | 10/2012 |
| WO | WO 2013082096 | | 6/2013 |
| WO | 2014089560 A1 | | 6/2014 |
| WO | 2016073634 A1 | | 5/2016 |

OTHER PUBLICATIONS

International Preliminary Report on Patentability dated May 9, 2017 in Application No. PCT/US2015/059080.
International Preliminary Report on Patentability dated Aug. 15, 2017 in Application No. PCT/US2016/017599.
Moros, et al., U.S. Appl. No. 15/432,567, filed Feb. 14, 2017 and entitled "Synergistic Combinations of Choline and Reactive Silanes in Antimicrobial Coatings".
Moros, et al., U.S. Appl. No. 15/432,413, filed Feb. 14, 2017 and entitled "Methods of Preparing Self-Decontaminating Surfaces Using Reactive Silanes, Triethanolamine and Titanium Anatase Sol".
Moros, et al., U.S. Appl. No. 15/432,428, filed Feb. 14, 2017 and entitled "Methods of Preparing Reactive Mixtures of Silanes and Triethanolamine and Polymers Therefrom".

(Continued)

Primary Examiner — Margaret G Moore
(74) Attorney, Agent, or Firm — Snell & Wilmer LLP.

(57) ABSTRACT

An anti-microbial coating formulation consisting essentially of triethanolamine and a silane.

11 Claims, 12 Drawing Sheets

(56) References Cited

OTHER PUBLICATIONS

Moros, et al., U.S. Appl. No. 15/432,443, filed Feb. 14, 2017 and entitled "Antimicrobial Coatings Formed by Reaction of Silanes With Triethanolamine to Form Polymeric Siloxanes".
Office Action dated Mar. 15, 2017 in U.S. Appl. No. 14/932,840.
Office Action dated Apr. 3, 2017 in U.S. Appl. No. 15/432,567.
WIPO; International Search Report and Written Opinion dated Feb. 23, 2016 in Application No. PCT/US2015/059080.
USPTO; Restriction Requirement dated Dec. 22, 2016 in U.S. Appl. No. 14/932,840.
Final Office Action dated Jun. 30, 2017 in U.S. Appl. No. 15/432,567.
Final Office Action dated Aug. 9, 2017 in U.S. Appl. No. 14/932,840.
Database WPI, Week 201401, Thomson Scientific, London, GB, AN 2013-V80024, XP002757772, -& CN 103 305 029 A (Univ South China Technology) Sep. 18, 2013.
International Search Report and Written Opinion dated May 27, 2016 for PCT/US2016/017599.
Notice of Allowance dated Oct. 24, 2017 in U.S. Appl. No. 14/932,840.
Moros, et al., U.S. Appl. No. 15/718,997, filed Sep. 28, 2017 and entitled "Antimicrobial Coatings Capable of Reducing the Number of Murine Norovirus Inoculated Thereon".
Moros, et al., U.S. Appl. No. 15/720,835, filed Sep. 29, 2017 and entitled "Methods of Coating a Surface With an Antimicrobial Coating Capable of Reducing the Number of Murine Norovirus Inoculated Thereon".
Notice of Allowance dated Sep. 8, 2017 in U.S. Appl. No. 15/432,567.
Examination Report dated Sep. 28, 2017 in Australian Application No. 2015343153.

\* cited by examiner

*The C-diff that occurred on September 19, 2013 was more than 13 weeks after the application
ABS' application was applied mid-June

TABLE 5

| | | Untreated | | ABS-G2015E – No TiO2 | | ABS-G2020E – No TiO2 | | ABS-G2030E – No TiO2 | |
|---|---|---|---|---|---|---|---|---|---|
| | | A | B | A | B | A | B | A | B |
| | | \multicolumn{8}{c|}{CFU/mL} | | | | | | | |
| 0 hour | 1.E+04 | 1.36E+07 | 9.70E+06 | 5.20E+06 | 1.13E+07 | 1.50E+07 | 2.60E+07 | 6.20E+06 | 1.10E+07 |
| | 1.E+05 | 1.60E+07 | 9.00E+06 | 4.00E+06 | 2.00E+06 | 0.00E+00 | 2.00E+03 | 4.00E+06 | 0.00E+00 |
| | 1.E+01 | | | | | 0.00E+00 | 0.00E+00 | 0.00E+00 | 0.00E+00 |
| | 1.E+02 | | | | | 0.00E+00 | 0.00E+00 | 0.00E+00 | 0.00E+00 |
| | 1.E+03 | | | | | 0.00E+00 | 0.00E+00 | 0.00E+00 | 0.00E+00 |
| 1 hour | 1.E+04 | 1.30E+07 | 9.10E+06 | 1.90E+06 | 2.60E+06 | 0.00E+00 | 0.00E+00 | 0.00E+00 | 0.00E+00 |
| | 1.E+05 | | | | | 0.00E+00 | 0.00E+00 | 0.00E+00 | 0.00E+00 |
| | 1.E+01 | | | 1.00E+02 | 3.00E+02 | 0.00E+00 | 1.00E+02 | 0.00E+00 | 0.00E+00 |
| 4 hour | 1.E+02 | | | | 1.50E+04 | 0.00E+00 | 0.00E+00 | 0.00E+00 | 0.00E+00 |
| | 1.E+03 | 3.70E+06 | 3.40E+06 | | | 0.00E+00 | 0.00E+00 | 0.00E+00 | 0.00E+00 |
| | 1.E+04 | | | | | 0.00E+00 | 0.00E+00 | 0.00E+00 | 0.00E+00 |
| | 1.E+05 | | | | | 0.00E+00 | 0.00E+00 | 0.00E+00 | 0.00E+00 |

FIG. 4

TABLE 6

| | ABS-G2015E – No TiO2 | ABS-G2020E – No TiO2 | ABS-G2030E – No TiO2 |
|---|---|---|---|
| | Log Reduction | | |
| 0 hour | 0.33 | -0.23 | 0.23 |
| 1 hour | 0.69 | 4.74 | 7.04 |
| 4 hour | 2.84 | 5.55 | 6.55 |

FIG. 5

TABLE 7

| | ABS-G2015H | ABS-G2020H | ABS-G2030H |
|---|---|---|---|
| | Percent Reduction | | |
| 0 hour | 53.42% | -69.77% | 41.48% |
| 1 hour | 79.64% | 100.00% | 100.00% |
| 4 hour | 99.86% | 100.00% | 100.00% |

FIG. 6

TABLE 8

CFU/mL

| | | Untreated | | ABS-G2015E | | ABS-G2020E | | ABS-G2030E | |
|---|---|---|---|---|---|---|---|---|---|
| | | A | B | A | B | A | B | A | B |
| 0 hour | 1.E+04 | 3.08E+07 | 4.80E+06 | | 4.10E+07 | 2.58E+07 | 1.66E+07 | | 2.00E+07 |
| | 1.E+05 | 1.97E+08 | 2.30E+07 | 3.10E+07 | | 2.60E+07 | 3.40E+07 | 2.10E+07 | 0.00E+00 |
| 1 hour | 1.E+01 | | | | | 8.00E+02 | 0.00E+00 | 0.00E+00 | 0.00E+00 |
| | 1.E+02 | | | | | 1.00E+03 | 0.00E+00 | 0.00E+00 | 0.00E+00 |
| | 1.E+03 | | | | | 0.00E+00 | 0.00E+00 | 0.00E+00 | 0.00E+00 |
| | 1.E+04 | 2.90E+06 | 6.40E+06 | 2.70E+06 | 3.80E+06 | 1.00E+02 | 0.00E+00 | 0.00E+00 | 0.00E+00 |
| 4 hour | 1.E+01 | | | 1.63E+04 | 6.20E+04 | 0.00E+00 | 0.00E+00 | 0.00E+00 | 0.00E+00 |
| | 1.E+02 | 2.70E+06 | 1.90E+05 | 2.70E+04 | 8.00E+04 | 0.00E+00 | 0.00E+00 | 0.00E+00 | 0.00E+00 |
| | 1.E+03 | | | 7.00E+04 | | 0.00E+00 | 0.00E+00 | 0.00E+00 | 0.00E+00 |
| | 1.E+04 | 1.30E+07 | 1.70E+06 | 2.00E+05 | 1.00E+05 | 0.00E+00 | 0.00E+00 | 0.00E+00 | 0.00E+00 |

FIG. 7

TABLE 9

| | Control | ABS-G2015E | ABS-G2020E | ABS-G2030E |
|---|---|---|---|---|
| | | Log Reduction from Time Zero | | |
| 0 hour | N/A | 0.25 | 0.40 | 0.49 |
| 1 hour | 1.14 | 1.29 | 5.33 | 7.81 |
| 4 hour | 1.16 | 2.91 | 6.71 | 7.81 |

FIG. 8

TABLE 10

| | Control | ABS-G2015E | ABS-G2020E | ABS-G2030E |
|---|---|---|---|---|
| | | Percent Reduction from Time Zero | | |
| 0 hour | N/A | 43.66% | 59.94% | 67.92% |
| 1 hour | 92.72% | 94.91% | 99.9995% | 99.999998% |
| 4 hour | 93.12% | 99.88% | 99.99998% | 99.999998% |

FIG. 9

TABLE 11

| | | Untreated | | ABS-G2015H | | ABS-G2020H | | ABS-G2030H | |
| --- | --- | --- | --- | --- | --- | --- | --- | --- | --- |
| | | A | B | A | B | A | B | A | B |
| 0 hour | 1.E+04 | 6.00E+05 | 4.00E+05 | 5.00E+05 | 4.00E+05 | 1.00E+06 | 8.00E+05 | 1.00E+05 | 1.00E+05 |
| | 1.E+05 | 2.00E+06 | 2.00E+06 | 0.00E+00 | 0.00E+00 | 0.00E+00 | 1.00E+06 | 0.00E+00 | 0.00E+00 |
| 1 hour | 1.E+01 | | | | | | | | |
| | 1.E+02 | | | | | | | | |
| | 1.E+03 | 9.00E+05 | 1.58E+06 | 9.10E+05 | 6.70E+05 | 2.00E+05 | 5.70E+05 | 0.00E+00 | 0.00E+00 |
| | 1.E+04 | 1.40E+06 | 1.70E+06 | 1.20E+06 | 3.00E+05 | 2.00E+05 | 9.00E+05 | 0.00E+00 | 0.00E+00 |
| | 1.E+05 | 0.00E+00 | 0.00E+00 | 4.00E+06 | 0.00E+00 | 0.00E+00 | 0.00E+00 | 0.00E+00 | 0.00E+00 |
| 4 hour | 1.E+01 | | | | | | | | |
| | 1.E+02 | | | | | | | | |
| | 1.E+03 | 1.28E+06 | 4.80E+05 | 1.00E+04 | 4.00E+04 | 0.00E+00 | 0.00E+00 | 0.00E+00 | 0.00E+00 |
| | 1.E+04 | 8.00E+05 | 4.00E+05 | 0.00E+00 | 0.00E+00 | 0.00E+00 | 0.00E+00 | 0.00E+00 | 0.00E+00 |
| | 1.E+05 | 1.00E+06 | 1.00E+06 | 0.00E+00 | 0.00E+00 | 0.00E+00 | 0.00E+00 | 0.00E+00 | 0.00E+00 |

CFU/mL

FIG. 10

TABLE 12

| | Log Reduction | | |
|---|---|---|---|
| | ABS-G2015H | ABS-G2020H | ABS-G2030H |
| 0 hour | 0.74 | 0.25 | 1.40 |
| 1 hour | -0.10 | 0.47 | 5.97 |
| 4 hour | 2.00 | 5.92 | 5.92 |

FIG. 11

TABLE 13

| | ABS-G2015H | ABS-G2020H | ABS-G2030H |
|---|---|---|---|
| | Percent Reduction | | |
| 0 hour | 82.00% | 44.00% | 96.00% |
| 1 hour | -26.88% | 66.49% | 100.00% |
| 4 hour | 98.99% | 100.00% | 100.00% |

FIG. 12

ANTI-MICROBIAL COATING AND METHOD TO FORM SAME

CROSS-REFERENCE TO RELATED APPLICATIONS

This is a Non-Provisional claiming priority to, and the benefit of, a U.S. Provisional Application having Ser. No. 62/114,998, filed Feb. 11, 2015, and a U.S. Non-Provisional Application having Ser. No. 14/932,840, filed Nov. 4, 2015, which are hereby incorporated by reference herein.

FIELD OF THE INVENTION

Embodiments generally relate an anti-microbial coating composition, and a method using that coating composition. In certain embodiments, the coating composition comprises a photocatalyst. In certain embodiments, the photocatalyst comprises a titanyl-oxide moiety. In certain embodiments, the coating composition comprises a silane.

BRIEF DESCRIPTION OF THE DRAWINGS

The invention will be better understood from a reading of the following detailed description taken in conjunction with the drawings in which like reference designators are used to designate like elements, and in which:

FIG. 4 sets forth TABLE 5, which recites CFU/mL data for each of three coating formulations that did not include one or more titanium-oxide moieties;

FIG. 5 sets forth TABLE 6, which recites Log Reduction data for each of three coating formulations that did not include one or more titanium-oxide moieties;

FIG. 6 sets forth TABLE 7, which recites Percent Reduction data for three formulations that did not include one or more titanium-oxide moieties;

FIG. 7 sets forth TABLE 8, which recites anti-microbial efficacy data for an electrostatic spray embodiment;

FIG. 8 sets forth TABLE 9, which recites anti-microbial efficacy data for an electrostatic spray embodiment;

FIG. 9 sets forth TABLE 10, which recites anti-microbial efficacy data for an electrostatic spray embodiment;

FIG. 10 sets forth TABLE 11, which recites anti-microbial efficacy data for a non-electrostatic spray embodiment;

FIG. 11 sets forth TABLE 12, which recites anti-microbial efficacy data for a non-electrostatic spray embodiment; and FIG. 12 sets forth TABLE 13, which recites anti-microbial efficacy data for a non-electrostatic spray embodiment.

DETAILED DESCRIPTION OF THE PREFERRED EMBODIMENTS

Figure 1:
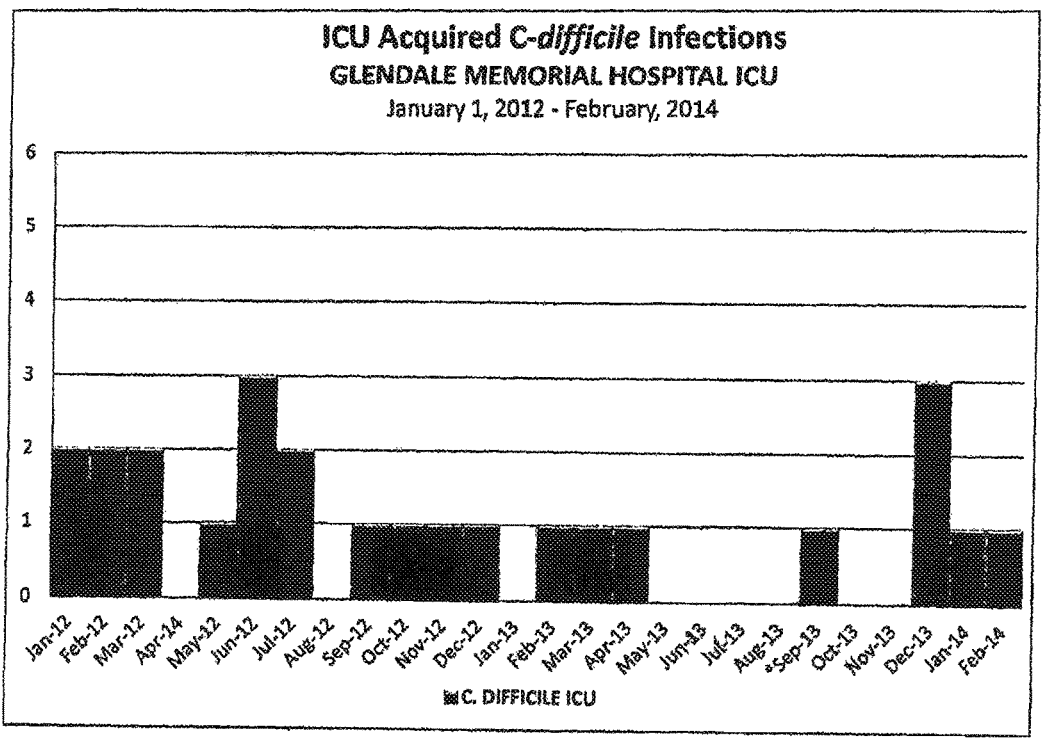
FIG. 1 graphically shows the number of hospital acquired C-difficile infections in the Glendale Memorial Hospital ICU from January 2012 through February 2014.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In certain embodiments of Inventors' composition and method, a coating is formed on a surface, where that coating comprises a plurality of silicon-oxygen bonds. In certain embodiments of Inventors' composition and method, a coating is formed on a surface, where that coating comprises a plurality of titanium-oxygen bonds in combination with a plurality of silicon-oxygen bonds.

In certain embodiments, a coating comprising a plurality of titanyl-oxide bonds in combination with a plurality of silicon-oxygen bonds is formed by disposing on a surface a silane in combination with one or more compounds comprising one or more titanyl-oxygen bonds. In certain embodiments, a coating comprising a plurality of titanyl-oxide bonds in combination with a plurality of silicon-oxygen bonds is formed by first disposing one or more compounds comprising one or more titanyl-oxygen bonds on the surface, and by disposing a silane onto the surface and over the one or more compounds comprising one or more titanyl-oxygen bonds. In certain embodiments, a coating comprising a plurality of titanyl-oxide bonds in combination with a plurality of silicon-oxygen bonds is formed by simultaneously disposing one or more compounds comprising one or more titanyl-oxygen bonds and a silane onto the surface.

In certain embodiments, Inventors' silane comprises compound 1.

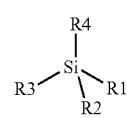

In certain embodiments, R1 is selected from the group consisting of OH and O-Alkyl. In certain embodiments, R2 is selected from the group consisting of OH and O-Alkyl. In certain embodiments, R3 is selected from the group consisting of OH and O-Alkyl. In certain embodiments, R4 is selected from the group consisting of OH, O-Alkyl, Alkyl, substituted Alkyl including γ-chloro-propyl, γ-amino-propyl, and quarternary ammonium salt-substituted Alkyl.

In certain embodiments, Inventors' silane comprises a trihydroxy silane 2.

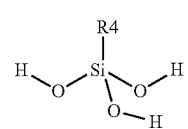

In certain embodiments, Inventors' silane comprises a silanetriol 2, wherein R4 is alkyl. In other embodiments, Inventors' silane comprises a silanetriol 2, wherein R4 is alkyl with an amino moiety. In yet other embodiments, Inventors' silane comprises a silanetriol 2, wherein R4 is alkyl with a chlorine substituent. In still other embodiments, Inventors' silane comprises a silanetriol 2, wherein R4 is alkyl with a quarternary ammonium group.

A silsesquioxane is an organosilicon compound 3 where Si represents the element silicon and O represents the element oxygen.

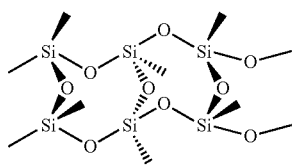

3

In certain embodiments, after application of Inventors' silane 1 or 2 to either a hard surface, i.e. wall, door, table, and the like, or a soft surface, i.e. bedding, draperies, furniture cushions, and the like, a resulting coating disposed on the hard surface/soft surface comprising a plurality of silsesquioxane structures. In certain embodiments, after application of Inventors' silane 1 or 2, in combination with one or more compounds comprising a titanyl-oxygen moiety, to either a hard surface, i.e. wall, door, table, and the like, or a soft surface, i.e. bedding, draperies, furniture cushions, and the like, a resulting coating disposed on the hard surface/soft surface comprises a plurality of silsesquioxane structures 3 in combination with plurality of titanyl-oxide structures.

Oxidation is a loss of electrons or an increase in oxidation state by a molecule, atom or ion. Substances that have the ability to oxidize other substances are said to be oxidative or oxidizing and are known as oxidizing agents, oxidants, or oxidizers. Put another way, the oxidant removes electrons from another substance, and is thus itself reduced. And, because it "accepts" electrons, it is also called an electron acceptor.

In chemistry, photocatalysis is the acceleration of a photoreaction in the presence of a catalyst. In catalyzed photolysis, light is absorbed by an adsorbed substrate. In photogenerated catalysis, the photocatalytic activity (PCA) depends on the ability of the catalyst to create electron-hole pairs, which generate free radicals (hydroxyl radicals: .OH) able to undergo secondary reactions. Its comprehension has been made possible ever since the discovery of water electrolysis by means of the titanium dioxide.

Certain titanyl-oxide morphologies exhibit photocatalytic characteristics when exposed to Ultra Violet (UV) light. When exposed to UV light, Inventors' Titanyl-Oxide Moieties create electron-hole pairs which generate free radical (e.g., hydroxyl radicals). The degree of photocatalytic strength varies depending on the type of titanyl-oxide, for example anatase titanium oxide (particle size of about 5 to 30 nanometers) is a stronger photocatalyst than rutile titanium oxide (particle size of about 0.5 to 1 microns).

In certain embodiments of Inventors' composition and method, a coating is formed on a surface, where that coating comprises a plurality of titanyl-oxide bonds, where that coating is formed by disposing Inventors' Titanyl-Oxide Moieties onto a target surface.

In certain embodiments of Inventors' composition and method, a coating is formed on a surface, where that coating comprises a plurality of silicon-oxygen bonds, where that coating is formed by disposing Inventors' silane 1 onto the surface.

In certain embodiments of Inventors' composition and method, a coating is formed on a surface, where that coating comprises a plurality of titanyl-oxide bonds, where that coating is formed by disposing on the surface a mixture of Peroxotitanium acid solution and Peroxo-modified anatase sol (collectively "Titanyl-Oxide Moieties").

In certain embodiments, Inventors' Titanyl-Oxide Moieties comprises up to about a total of one weight percent loading of the mixture of Peroxotitanium acid solution and Peroxo-modified anatase sol. In certain embodiments, Inventors' Titanyl-Oxide Moieties comprises about 0.5 weight percent Peroxotitanium acid solution in combination with about 0.5 weight percent Peroxo-modified anatase sol.

Figure 3:
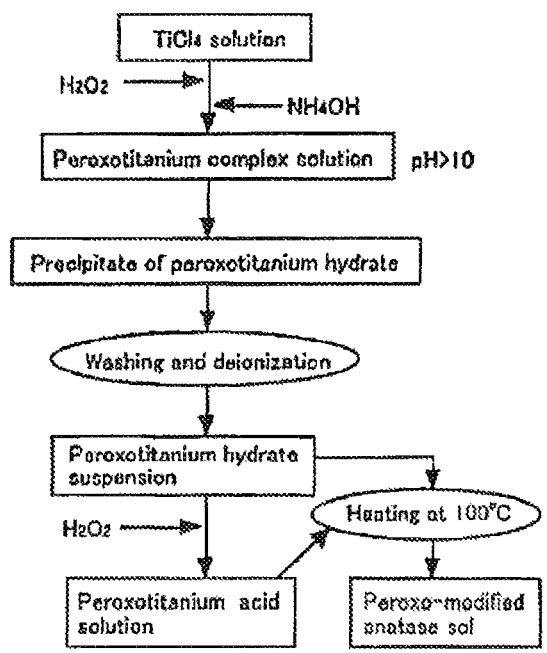
FIG. 3 shows a flowchart of a synthetic procedure for both Peroxotitanium acid solution and Peroxo-modified anatase sol.

A method to prepare both Peroxotitanium acid solution and Peroxo-modified anatase sol is disclosed in Journal of Sol-Gel Science and Technology, September 2001, Volume 22, Issue 1-2, pp 33-40. This publication discloses, inter alia, the reaction scheme, shown in FIG. 3, which summarizes the synthetic procedure for both Peroxotitanium acid solution and Peroxo-modified anatase sol.

In the following examples, reference is made to coatings ABS-G2015, ABS-G2020, and ABS-G2030. Coating formulation ABS-G2015 comprises a silicone-containing compound having structure V:

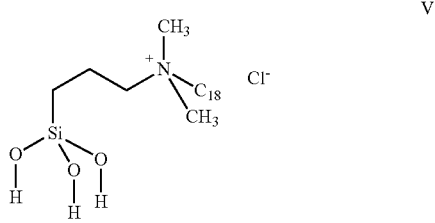

Coating formulation ABS-G2015 further comprises the Titanyl-Oxide Moieties. The order of deposition onto a surface is not critical. In certain embodiments, the silicone-containing compound is first disposed on a surface, and the Titanyl-Oxide Moieties are disposed over that silicone-containing compound. In other embodiments, the Titanyl-Oxide Moieties are first disposed on a surface, and the silicone-containing compound is disposed over that Titanyl-Oxide Moieties—treated surface. In yet other embodiments, the Titanyl-Oxide Moieties and the silicone-containing compound are first pre-mixed, and the resulting mixture is disposed on the surface of the substrate.

Coating formulation ABS-G2020 comprises a silicone-containing compound having structure VI:

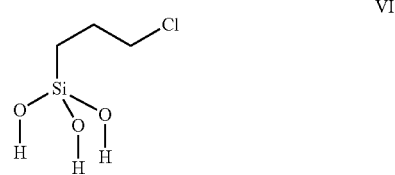

Coating formulation ABS-G2020 further comprises the Titanyl-oxide Moieties. The order of deposition onto a surface is not critical. In certain embodiments, the silicone-containing compound is first disposed on a surface, and the Titanyl-oxide Moieties are disposed over that silicone-containing compound. In other embodiments, the Titanyl-oxide Moieties are first disposed on a surface, and the silicone-containing compound is disposed over that Titanyl-oxide Moieties-treated surface. In yet other embodiments, the Titanyl-oxide Moieties and the silicone-containing compound are first pre-mixed, and the resulting mixture is disposed on the surface of the substrate.

Coating formulation ABS-G2030 comprises a silicone-containing compound having structure VII:

$$\text{VII}$$

Coating formulation ABS-G2030 further comprises the Titanyl-Oxide Moieties. The order of deposition onto a surface is not critical. In certain embodiments, the silicone-containing compound is first disposed on a surface, and the Titanyl-Oxide Moieties are disposed over that silicone-containing compound. In other embodiments, the Titanyl-Oxide Moieties are first disposed on a surface, and the silicone-containing compound is disposed over that Titanyl-Oxide Moieties-treated surface. In yet other embodiments, the Titanyl-Oxide Moieties and the silicone-containing compound are first pre-mixed, and the resulting mixture is disposed on the surface of the substrate.

The following Examples are presented to further illustrate to persons skilled in the art how to make and use the invention. These Examples are not intended as limitations, however, upon the scope of the invention.

Example 1

This Example 1 evaluates the anti-microbial efficacy of coatings ABS-G2015, ABS-G020, and ABS G-2030, against Murine Noro Virus. Murine norovirus (MNV) is a species of norovirus affecting mice. Norovirus is the most common cause of viral gastroenteritis in humans. It affects people of all ages. The virus is transmitted by, inter alia, aerosolization of the virus and subsequent contamination of surfaces. The virus affects around 267 million people and causes over 200,000 deaths each year; these deaths are usually in less developed countries and in the very young, elderly and immunosuppressed.

The test coupons of this Example 1 were prepared using the Procedure recited immediately hereinbelow.

Procedure

Put on sterile gloves.
Prepare the test coupons by wiping them first with Isopropyl Alcohol and allowing to dry.
Clean the test coupons with surface cleaner using a microfiber cloth.
Hold sprayer about eight (8) inches from surface to be cleaned.
Spray on let stand for 1-3 minutes and wipe it off, if the area is extremely dirty allow cleaner to stand longer, or apply a second spray and wipe.
Wipe surface with a clean, damp sponge or cloth.
Allow surface to completely dry.
With gloved hands examine coupons for consistency.
Prepare a 10 volume percent solution of the selected silane in Methanol (MeOH) (10 ml silane in 90 ml MeOH).
Prepare Triethanolamine as a 10 volume percent solution in MeOH.
Combine the triethanolamine solution and the silane solution in a 1:1 ratio on a stir plate at room temperature (ie-100 ml triethanolamine solution added to 100 ml silane solution).

Silane Application

Add the 1:1 silane/triethanolamine solution prepared about to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.
Optimal spraying distance is at least 36 to 48 inches away from the target surface.
Hold the spray gun at right angles to the target surface and spray.
Target surface should just barely glisten with the spray. Do not over-saturate the surface.
Allow target surface to dry, i.e. allow at least 90 weight percent of the methanol liquid carrier to evaporate to give a deposition consisting essentially of the selected silane and triethanolamine. The deposition onto the target surface consists of at least 33 volume percent of the selected silane, at least 33 volume percent of triethanolamine, and up to about 33 volume percent residual methanol carrier liquid.
Rinse spray gun with distilled water prior to applying Inventors' Titanyl-Oxide Moieties (unless using 2 sprayers, one for each product).

Titanyl-Oxide Moieties Application

Add an aqueous mixture of Inventors' Titanyl-Oxide Moieties to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.
Optimal spraying distance is at least 36 to 48 inches away from the target surface.
Hold the spray gun at right angles to the target surface and spray.
Target surface should just barely glisten with the spray. Do not over-saturate the surface.
Allow target surface to dry, i.e. allow at least 90 weight percent of the water liquid carrier to evaporate to give a deposition consisting essentially of Inventors' Titanyl-Oxide Moieties. The deposition onto the target surface consists of at least 66 volume percent of Inventors' Titanyl-Oxide Moieties and up to about 33 volume percent residual water carrier liquid.

Clean the spray gun with distilled water per manufactures' specifications after each day of use.

Tables 2 and 3 recite anti-microbial efficacy data four (4) hours after inoculation of the treated test coupons. Table 2 includes data for ABS-G2020 and ABS-G2030 treated Formica coupons. Table 3 includes data for ABS-G2020 and ABS G-2030 treated stain less steel coupons.

TABLE 1

Surface Time-Kill Study Evaluating Four Coating Formulations Against *Murine Norovirus*: Time Zero Data

| Test Organism | Contact Time | Sample ID[a] | Viral Counts (TCID$_{50}$ per mL) | Log$_{10}$ Reduction | Percent Reduction |
|---|---|---|---|---|---|
| *Murine norovirus* | Time Zero | Formica - Ctrl SS-Ctrl | 1.48E+07 6.76E+06 | N.A. | |

[a]SS: Stainless Steel

TABLE 2

Surface Time-Kill Study Evaluating Four Coating Formulations Against *Murine Norovirus*: 4 Hour Contact Time Data

| Test Organism | Contact Time | Sample ID[a] | Viral Counts (TCID$_{50}$ per mL) | Log$_{10}$ Reduction | Percent Reduction |
|---|---|---|---|---|---|
| *Murine norovirus* | 4 Hours | Ctrl (Formica) | 1.00E+05 | N.A. | |
| | | Ctrl (SS) | 6.76E+04 | | |
| | | ABS-G2015 (SS) | 6.76E+04 | 0.00 | 0% |
| | | ABS-G2020 (Form) | ≤3.16E+03 | ≥1.50 | ≥97% |
| | | ABS-G2030 (Form) | 6.76E+03 | 1.00 | 90% |

[a]SS: Stainless Steel; SW: SurfaceWise, Form: Formica
[b]"≤": No viral cytopathology observed beyond toxic levels; therefore titer at or below limit of detection

TABLE 3

Surface Time-Kill Study Evaluating Two Coating Formulations Against Murine Norovirus: 4 Hour Contact Time Data

| Test Organism | Contact Time | Sample ID[a] | Viral Counts (TCID$_{50}$ per mL) | Mean Viral Titer | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|---|---|
| *Murine norovirus* | 4 Hours | SS-Control (Rep A) | 6.76E+04 | 1.06E+05 | 1.47 | 97% | N.A. | |
| | | SS-Control (Rep B) | 1.45E+05 | | | | | |
| | | ABS-G2020 (Rep A) | 1.00E+04 | 1.57E+04 | 2.30 | 99.5% | 0.83 | 85.2% |
| | | ABS-G2020 (Rep B) | 2.14E+04 | | | | | |
| | | ABS-G2030 (Rep A) | 4.68E+03 | ≤3.92E+03 | ≥2.91 | ≥99.8% | ≥1.43 | ≥96.3% |
| | | ABS-G2030 (Rep B) | ≤3.16E+03 | | | | | |

[a]SS: Stainless Steel
[b]"≤": No viral cytopathology observed beyond toxic levels; therefore titer at or below limit of detection

TABLE 4

Surface Time-Kill Study Evaluating Two Coating Formulations Against Murine Norovirus: 6 Hour Contact Time Data

| Test Organism | Contact Time | Sample ID[a] | Viral Counts (TCID$_{50}$ per mL) | Mean Viral Titer | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|---|---|
| *Murine norovirus* | 6 Hours | SS-Control (Rep A) | 3.16E+04 | 4.96E+04 | 1.80 | 98% | N.A. | |
| | | SS-Control (Rep B) | 6.76E+04 | | | | | |
| | | ABS-G2020 (Rep A) | 1.00E+04 | 8.38E+03 | 2.58 | 99.7% | 0.77 | 83.1% |
| | | ABS-G2020 (Rep B) | 6.76E+03 | | | | | |
| | | ABS-G2030 (Rep A) | 4.68E+03 | ≤3.92E+03 | ≥2.91 | ≥99.8% | ≥1.10 | ≥92.1% |
| | | ABS-G2030 (Rep B) | ≤3.16E+03 | | | | | |

[a]SS: Stainless Steel
[b]"≤": No viral cytopathology observed beyond toxic levels; therefore titer at or below limit of detection 1. RAW (mouse macrophage) host cells were prepared in 96-well trays 24 hours prior to use in testing.
2. On the day of testing, a stock vial of test virus, murine norovirus, was removed from storage at −80° C. (titer=5× $10^8$ $TCID_{50}$ units per ml). An organic soil load (heat-inactivated fetal bovine serum) was added to obtain a final concentration of 5%.
3. Control (non-coated stainless steel and formica) and coated test carriers [ABS-G2015 (SS); ABS-G2020 (Form); ABS-G2030 (Form); ABS-P2015 (SS)] were placed into sterile Petri dishes (one per dish) using pre-sterilized forceps.
4. Viral inocula (0.010 ml) were pipetted onto the center of the control and test carriers, and spread over a surface area of ~1-$in^2$ using a sterile, bent pipette tip.
5. One set of control carriers (per surface material type) was harvested/neutralized immediately to determine Time Zero counts by placement into sterile stomacher bags containing 3 ml of neutralizing solution (calf serum supplemented with 0.001% Na-thiosulfate and 0.001% Na-thioglycollate). The bags were stomached for 120 seconds at high speed to release the viruses from the carriers.
6. The remaining control and test carriers were held under ambient conditions for the duration of each of the specified study contact times of 4 hours and 24 hours [placement distance/configuration: ~68 inches (~1.7 m) below two full-spectrum bulbs, inoculated side facing up towards the lights)]. All carriers were observed to be dried within 10 minutes of inoculation.
7. Upon closure of the respective contact times, the control and test carriers were neutralized by placement into sterile stomacher bags containing 3 ml of neutralizing solution, followed by stomaching as previously described.
8. At the start and finish of each of the contact times, room temperature, relative humidity, and illuminance (lux) were measured and recorded.
9. Control and test carrier eluates were serially diluted (1:10) and plated in replicates of six onto RAW host cells prepared to the appropriate confluency.
10. The plates were observed every 24 to 48 hours to visualize viral cytopathic effects (CPE) and cytotoxicity.
11. Following a 9-day assay incubation period, the plates were formally scored.
12. $Log_{10}$ and percent reductions were calculated for each of the test coating formulations relative to the timed control virus counts (per surface type). However, reductions could not be computed for the 24 hour contact time due to insufficient viral recovery from the control carriers.
13. A neutralization validation was performed for each of the test coating formulations (except for ABS-P2015 due to a lack of carriers). One control carrier and one of each test carrier type were placed into stomacher bags containing 3 ml of neutralizer, and processed as previously described. The eluate was serially diluted, and low titer inoculum of the test virus (~3-$log_{10}$) was added to each of the dilution tubes per control and test carrier suspension. Aliquots (0.1 ml) of the suspensions were then plated in order to assess cytotoxic levels of the neutralized test materials.

Example 2

This Example 2 utilizes the three (3) silanes utilized in coating formulations, namely ABS-G2015, ABS-G2020, and ABS-G2030, but without any Titanyl-Oxide containing compounds. The method of Example 1 discussed above relating to spray deposition of a silane onto test coupons was utilized in this Example 2. The portion of Example 1 relating to Titanyl-Oxide Moieties Application was not utilized in this Example 2.

TABLE 5, set forth in FIG. 4, recites CFU/mL data for each of the three coating formulations, wherein each formulation did not include one or more titanium-oxide moieties. TABLE 6, set forth in FIG. 5, recites Log Reduction data for the three formulations evaluated, wherein each formulation did not include one or more titanium-oxide moieties. TABLE 7, set forth in FIG. 6, recites Percent Reduction data for the three formulations utilized, wherein each formulation did not include one or more titanium-oxide moieties.

Example 3

This Example 3 utilizes complete formulations ABS-G2015, AB-G2020, and ABS-G2030, where those coating formulations were disposed on stainless steel test coupons using the full procedure of Example 1. In one set of experiments, the formulations were disposed onto the test coupons using an electrostatic spray assembly. In another set of experiments, the formulations were disposed onto the test coupons using a non-electrostatic spray assembly.

Tables 8, 9, and 10, set forth in FIG. 7, FIG. 8 and FIG. 9, respectively, recite anti-microbial efficacy data for the electrostatic spray embodiments. Tables 11, 12, and 13, set forth in FIG. 10, FIG. 11 and FIG. 12, respectively, recite anti-microbial efficacy data for the non-electrostatic spray embodiments.

Example 4

A study was conducted at the Glendale Memorial Hospital and Health Center in Glendale, Calif. (the "Glendale Memorial Hospital Study"). The Center has a 24 bed intensive care (ICU). The study was performed between May 10 and Sep. 30, 2013. The Glendale Memorial Hospital Study was designed to assess the anti-microbial efficacy of coating composition ABS-G2015, described hereinabove, where that coating composition was applied using the complete method of Example 1 herein.

In the Glendale Memorial Hospital Study, the entire ICU was subjected to the two step spray regime described herein to treat all surfaces in each room including hard surfaces (beds, tray tables, bed rail, walls, etc.) and soft surfaces (drapes, cloth and vinyl covered chairs, etc.). More specifically, each surface was first electrostatically spray coated at room temperature using an aqueous composition formed by mixing Octadecylaminodimethyltrihydroxysilylpropyl Ammonium Chloride (the "Silylated Quarternary Amine") at about 3.6 weight percent in water.

After about fifteen (15) minutes after the electrostatic spray coating using the aqueous Silylated Quarternary Amine, each surface was then electrostatically coated at room temperature using the Titanyl-Oxide Moieties described hereinabove.

The treated surfaces were maintained at room temperature during the spray deposition of the aqueous Silylated Quarternary Amine, and during the spray deposition of the Titanyl-Oxide Moieties. None of the treated surfaces were subjected to any elevated heat treatment wherein the treated surface was heated to a temperature greater than about room temperature after completion of the two step coating regime.

Ninety-five (95) specific sites in the ICU were selected for recurring sampling at weeks 1, 2, 4, 8, and 15, after the two step spraying regime. Those selected sites included bed rails, bed controls, tray tables, and walls above sinks. Samples were also collected from the two ICU nursing stations and waiting lobby including countertops, phones, computer keyboards, chair armrests and end tables. All movable items were inconspicuously tagged and coded over the course of the study so that the same objects could be sampled.

Areas of 100 cm$^2$ were sampled using a sponge stick containing Letheen broth (3M, St. Paul, Minn.) to neutralize any residual disinfectant. After collection the samples were immediately placed on ice packs and sent overnight to the University of Arizona for analysis by Professor Charles Gerba.

FIG. 1 hereto is a true and accurate copy of a first graph provided by the Manager, Infection Prevention, Dignity Health/Glendale Memorial Hospital & Health Center. Exhibit 1 graphically shows the number of hospital acquired *C-difficile* infections in the Glendale Memorial Hospital ICU from January 2012 through February 2014.

FIG. 1 indicates that with the exception of September 2013, there were no hospital acquired *C-difficile* infections originating in the ICU during the period May 2013 through November 2013. Thus, FIG. 1 shows that there was a single hospital acquired *C-difficile* infection originating in the ICU during the six month period May 2013 through November 2013.

FIG. 1 further shows that, other than the six month period May 2013 through November 2013, there was no other 6 month period during the 25 months from January 2012 through February 2014 wherein only a single hospital acquired *C-difficile* infection originated in the ICU.

Figure 2:
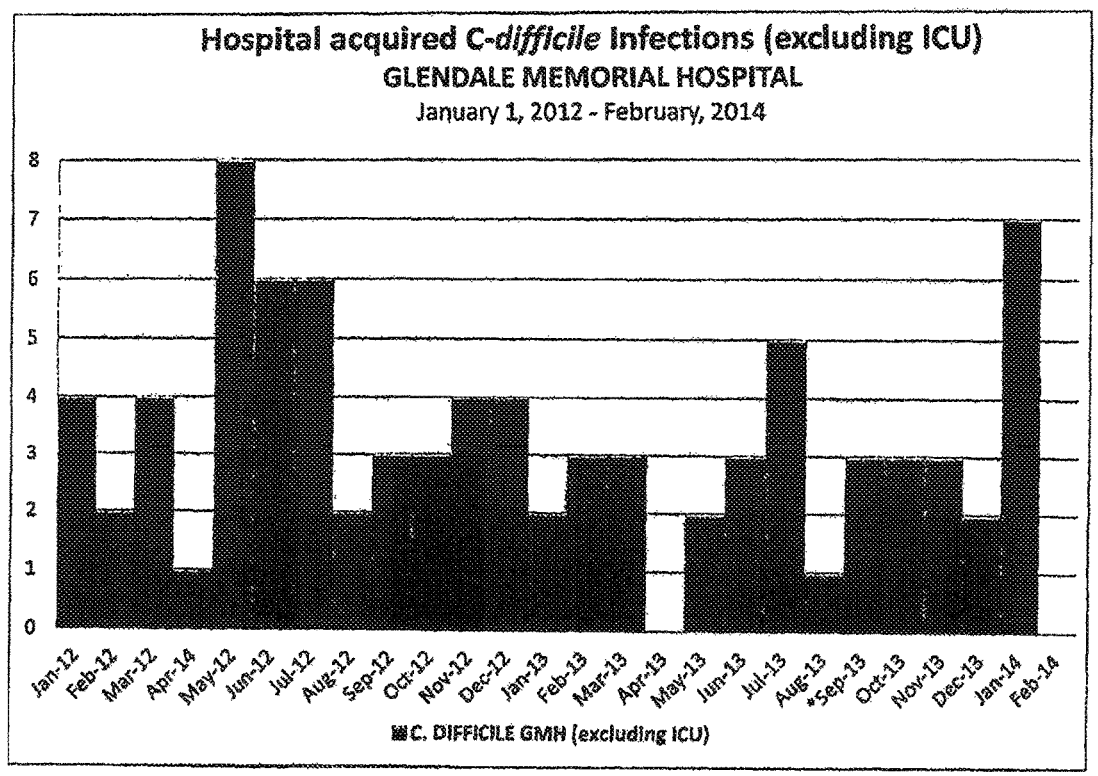
FIG. 2 graphically shows the number of hospital acquired C-difficile infections at the Glendale Memorial Hospital (excluding ICU) from January 2012 through February 2014.

All surfaces in the ICU were treated as described hereinabove during the first week of May 2013 as part of the Glendale Memorial Hospital Study. FIG. 2 hereto is a true and accurate copy of a second graph provided by the Manager, Infection Prevention, Dignity Health/Glendale Memorial Hospital & Health Center. Exhibit 2 graphically shows the number of hospital acquired *C-difficile* infections at the Glendale Memorial Hospital (excluding ICU) from January 2012 through February 2014.

FIG. 2 indicates that, with the exception of April 2013, there were between 1 and 8 hospital acquired *C-difficile* infections every month during the 25 month period in hospital areas outside of the ICU. During the period May 2013 through November 2013, FIG. 2 shows that there were a total of 20 hospital acquired *C-difficile* infections originating outside of the ICU at the Glendale Memorial Hospital.

FIGS. 1 and 2 show that during the period May 2013 through November 2013, a single hospital acquired *C-difficile* infection originated in the ICU at the Glendale Memorial Hospital, and a total of 20 hospital acquired *C-difficile* infections originated outside of the ICU at the Glendale Memorial Hospital.

*Clostridium difficile* colitis or pseudomembranous colitis is colitis (inflammation of the large intestine) resulting from infection with *Clostridium difficile*, a type of spore-forming bacteria. It causes an infectious diarrhea called *C. difficile* diarrhea. Latent symptoms of *Clostridium difficile* infection (CDI) often mimic some flu-like symptoms and may mimic disease flare-ups in people with inflammatory bowel disease-associated colitis. *C. difficile* releases toxins that may cause bloating and diarrhea, with abdominal pain, which may become severe.

*C. difficile* is transmitted from person to person by the fecal-oral route. The organism forms heat-resistant spores that are not killed by alcohol-based hand cleansers or routine surface cleaning. Thus, these spores survive in clinical environments for long periods. Because of this, the bacteria may be cultured from almost any surface.

*Clostridium difficile* spores are extremely hardy, and can survive for long amounts of time in environments devoid of food. The spores are resistant to drying and heating, and also have resistance to many forms of antiseptic cleaners. *C. diff* can also survive in spore form for as long as five months. The ability of *C. diff* to survive in this resistant form poses quite a challenge for hospitals.

Because *C. diff* forms heat-resistant spores that are not killed by alcohol-based hand cleansers or routine surface cleaning, the data of FIGS. 1 and 2 demonstrate that treatment of hard surfaces and soft surface in the Glendale Memorial Hospital ICU with ABS-G2015 necessarily reduced the occurrence of *C. diff* spores in that ICU. The data of FIG. 2 show that other hospital departments that were not treated with ABS-G2015 coating composition experienced a much greater level of hospital acquired *C. diff* infections, thereby corroborating the anti-microbial efficacy of the coating resulting from application of ABS-G2015 against *C. diff* spores.

In coating formulations ABS G2015, G2020, and G2030, depending on the stoichiometry of the mixture of triethanolamine and the organosilane, one or polymeric species are formed on a treated surface. In certain embodiments, and as shown in Reaction Scheme 2, triethanolamine 9 and organosilane 1 react to form a linear polymer 10, wherein n is greater than or equal to 1 and less than or equal to about 10.

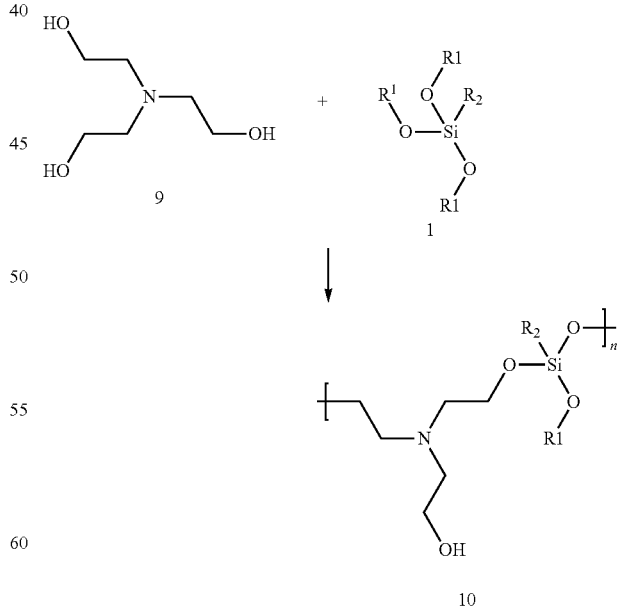

In other embodiments, and as shown in Reaction Scheme 3, triethanolamine 9 and organosilane 1 react to form a branched polymer 11.

REACTION SCHEME 3

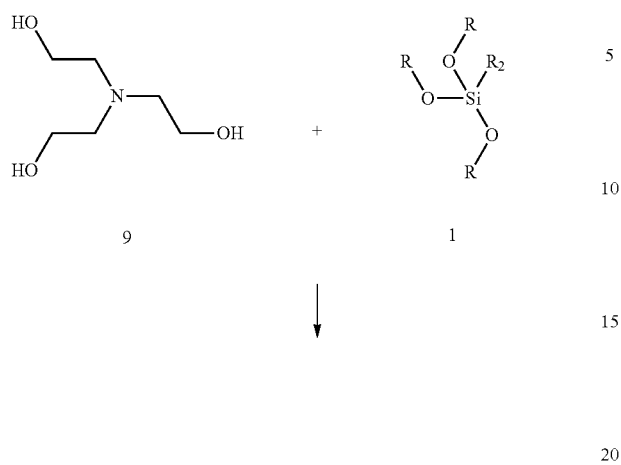

9    1

11

Wherein in Reaction Scheme 3, x is greater than or equal to 1 and less than or equal to about 10, and wherein y is greater than or equal to 1 and less than or equal to about 10.

In other embodiments, and as shown in Reaction Scheme 4, triethanolamine 9 and organosilane 1 react to form a cross-linked polymer 12.

REACTION SCHEME 4

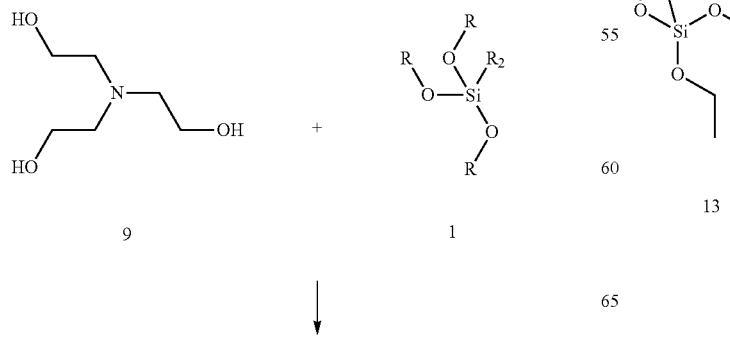

9    1

-continued

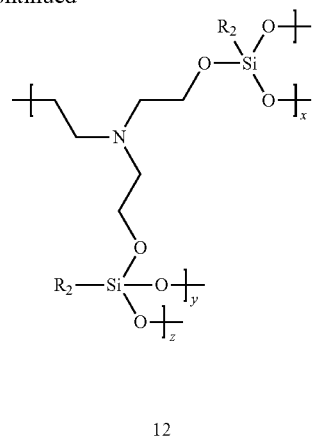

12

Wherein in Reaction Scheme 4, x is greater than or equal to 1 and less than or equal to about 10, and wherein y is greater than or equal to 1 and less than or equal to about 10, and wherein z is greater than or equal to 1 and less than or equal to about 10.

In certain embodiments, Inventors' organosilane comprises tetraethylorthosilicate 13. In certain embodiments and as shown in Reaction Scheme 5 and depending on the stoichiometry of the starting materials 9 and 13, Inventors' cross-linked polymeric material 14 is formed by reaction of tetraethylorthosilicate 13 and triethanolamine 9. Reaction Scheme 5 illustrates a single Si atom having four (4) different polymer chains originating therefrom. Those skilled in the art will appreciate that Inventors' cross-linked polymer material 14 comprises a very high cross-link density.

REACTION SCHEME 5

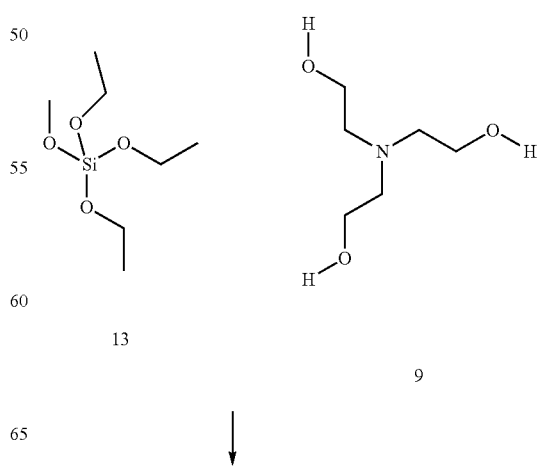

13    9

-continued

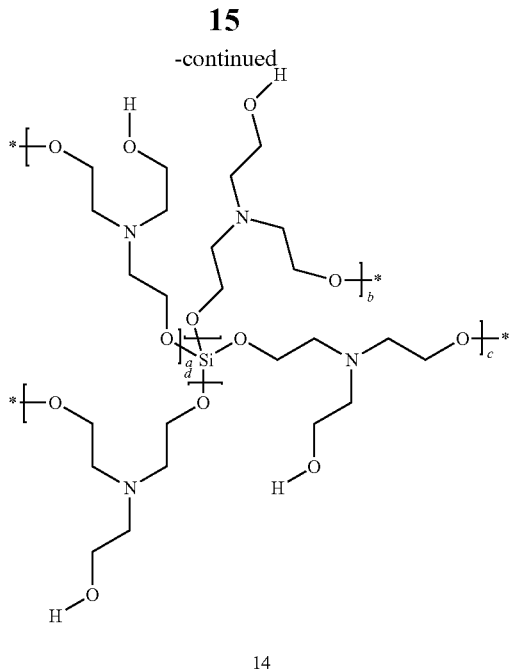

14

Wherein in Reaction Scheme 5, a is greater than or equal to 1 and less than or equal to about 10, and wherein b is greater than or equal to 1 and less than or equal to about 10, and wherein c is greater than or equal to 1 and less than or equal to about 10, and wherein d is greater than or equal to 1 and less than or equal to about 10.

In certain embodiments and as shown in Reaction Scheme 6 and depending on the stoichiometry of the starting materials 15 and 13, Inventors' cross-linked polymeric material 16 is formed by reaction of tetraethylorthosilicate 13 and diethanolamine 13. Reaction Scheme 6 illustrates a single Si atom having four (4) different polymer chains originating therefrom. Those skilled in the art will appreciate that Inventors' cross-linked polymer material 16 comprises a very high cross-link density.

REACTION SCHEME 6

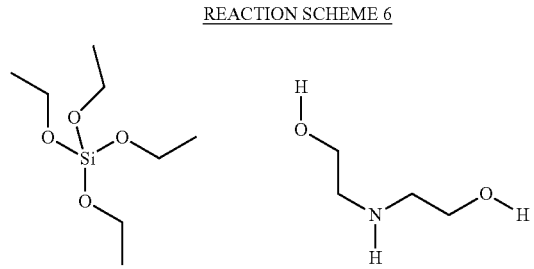

-continued

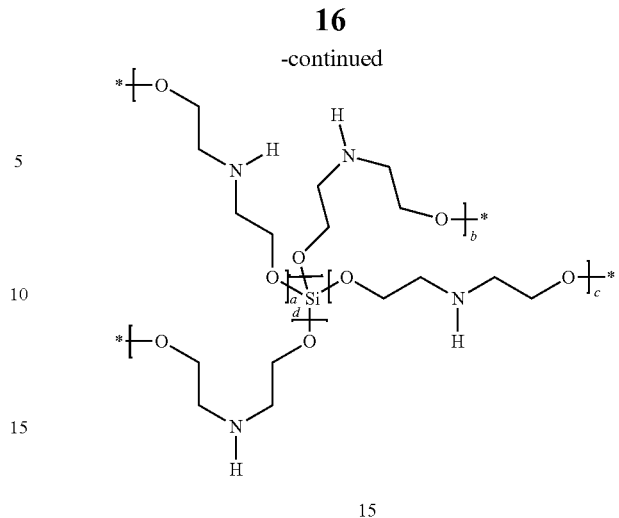

Wherein in Reaction Scheme 6, a is greater than or equal to 1 and less than or equal to about 10, and wherein b is greater than or equal to 1 and less than or equal to about 10, and wherein c is greater than or equal to 1 and less than or equal to about 10, and wherein d is greater than or equal to 1 and less than or equal to about 10.

While the preferred embodiments of the present invention have been illustrated in detail, it should be apparent that modifications and adaptations to those embodiments may occur to one skilled in the art without departing from the scope of the present invention.

We claim:

1. An antimicrobial coating formulation comprising:
89.48 vol. % methanol;
5.26 vol. % triethanolamine; and
5.26 vol. % of a silane having a structure:

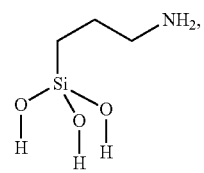

wherein the volume percentages are based on the total volume of the formulation.

2. The antimicrobial coating formulation of claim 1, wherein:
said antimicrobial coating formulation, when dried on a surface, exhibits a 6.5 log reduction in murine norovirus 4 hours after initial inoculation of murine norovirus on said surface.

3. The antimicrobial coating formulation of claim 2, wherein said surface is formed from stainless steel.

4. An antimicrobial coating formulation consisting essentially of:
a silane having a structure:

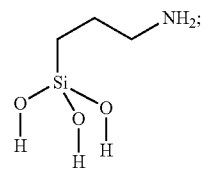

a mixture of Peroxotitanium acid and Peroxo-modified anatase sol;
and triethanolamine.

5. The antimicrobial coating formulation of claim 4, wherein:
said antimicrobial coating formulation, when dried on a surface, exhibits a ≥2.91 log reduction in murine norovirus 4 hours after initial inoculation of murine norovirus on said surface.

6. The antimicrobial coating formulation of claim 5, wherein said surface is formed from stainless steel.

7. The antimicrobial coating formulation of claim 2, wherein drying on a surface comprises allowing at least 90 wt. % of the methanol liquid carrier to evaporate to provide a deposition consisting essentially of said silane and triethanolamine.

8. A method to prepare an antimicrobial surface, comprising:
disposing on a surface an antimicrobial coating formulation comprising 5.26 vol. % triethanolamine, 89.48 vol % methanol, and 5.26 vol. % of a silane having a structure:

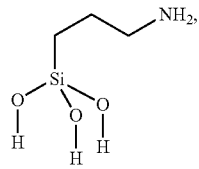

wherein the volume percentages are based on the total volume of the formulation;
allowing said methanol to evaporate to form a coating consisting essentially of said silane;
disposing a mixture of Peroxotitanium acid and Peroxo-modified anatase sol in a water carrier onto said surface; and
allowing said water carrier to evaporate to form a Titanyl-Oxide coating consisting essentially of said mixture of Peroxotitanium acid and Peroxo-modified anatase sol.

9. The method of claim 8, wherein:
said silane coating is first formed on said surface;
said Titanyl-Oxide coating is formed over said silane coating.

10. The method of claim 8, wherein:
said Titanyl-Oxide is first formed on said surface;
said silane coating is formed over said Titanyl-Oxide coating.

11. A method to prepare an antimicrobial surface, comprising:
disposing an antimicrobial coating formulation consisting essentially of a silane, triethanolamine, and a mixture of Peroxotitanium acid and Peroxo-modified anatase sol, in a liquid carrier on a surface, wherein said silane has the structure:

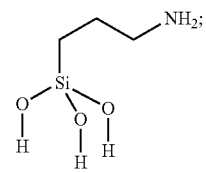

and
allowing said liquid carrier to evaporate.

* * * * *